US006029499A

United States Patent [19]

Sittler et al.

[11] Patent Number: 6,029,499

[45] Date of Patent: Feb. 29, 2000

[54] MODULAR GAS CHROMATOGRAPH

[75] Inventors: Fred C. Sittler, Excelsoir; Cynthia R. Nelson, Anoka; Lawrence R. Majerus, Chaska, all of Minn.

[73] Assignee: Rosemount Analytical Inc., Anaheim, Calif.

[21] Appl. No.: 09/081,418

[22] Filed: May 19, 1998

Related U.S. Application Data

[63] Continuation-in-part of application No. 08/566,133, Dec. 1, 1995, Pat. No. 5,808,179

[60] Provisional application No. 60/004,618, Sep. 29, 1995.

[51] Int. Cl.[7] .......... G01N 30/02

[52] U.S. Cl. .......... 73/23.42; 96/105

[58] Field of Search .......... 73/23.42, 23.39, 73/23.35, 23.41; 95/85, 86, 87, 82; 96/101, 105, 106; 422/89

[56] References Cited

U.S. PATENT DOCUMENTS

| | | | |
|---|---|---|---|
| 2,591,762 | 4/1952 | Zaikowski | 73/27 |
| 3,069,897 | 12/1962 | Claudy | 73/23.42 |
| 3,276,241 | 10/1966 | Hubner | 73/23 |
| 3,700,411 | 10/1972 | Davis | 23/254 |
| 4,044,593 | 8/1977 | Haruki et al. | 73/23.1 |
| 4,057,998 | 11/1977 | Moreaux | 73/23.1 |
| 4,410,632 | 10/1983 | Dilley et al. | 436/20 |
| 4,537,217 | 8/1985 | Allen, Jr. | 137/561 A |
| 4,712,008 | 12/1987 | Vora et al. | 250/287 |
| 4,741,198 | 5/1988 | Farren et al. | 73/23.4 |
| 4,842,825 | 6/1989 | Martin et al. | 422/80 |
| 4,888,295 | 12/1989 | Zaromb et al. | 436/161 |
| 4,909,078 | 3/1990 | Sittler et al. | 73/23.35 X |
| 5,071,547 | 12/1991 | Cazer et al. | 210/198.2 |
| 5,105,652 | 4/1992 | Manfredi et al. | 73/23.25 |
| 5,236,668 | 8/1993 | Higdon | 422/89 |
| 5,298,225 | 3/1994 | Higdon | 422/89 |
| 5,313,061 | 5/1994 | Drew et al. | 250/281 |
| 5,340,543 | 8/1994 | Annino et al. | 422/89 |
| 5,341,841 | 8/1994 | Schaefer | 137/561 A |
| 5,356,594 | 10/1994 | Neel et al. | 422/54 |
| 5,376,335 | 12/1994 | Gleaves | 422/80 |
| 5,426,300 | 6/1995 | Voss et al. | 250/288 |
| 5,583,281 | 12/1996 | Yu | 73/23.42 |
| 5,741,960 | 4/1998 | Payne et al. | 73/23.41 |
| 5,808,179 | 9/1998 | Sittler et al. | 73/23.42 |

FOREIGN PATENT DOCUMENTS 0 636 882 A1 1/1995 European Pat. Off. .

OTHER PUBLICATIONS

"SGC 3000 Smart Gas Chromatograph", Yamatake–Honeywell Co. Ltd., Industrial Systems Division, Totate International Bldg., 2–12–19, Shibuya, Shibuya–ku, Tokyo, 150, Japan. 1989.

"A Gas Chromatographic Air Analyzer Fabricated on a Silicon Wafer", by Stephen c. Terry, John H. Jerman and James B. Angell, *IEEE Transactions on Electronic Devices*, vol. Ed–26, No. 12, Dec. 1979, pp. 1880–1886.

"A Miniature Gas Chromatograph For Atmospheric Monitoring", by J.H. Jerman and S.C. Terry, *Environment Internationa*, vol. 5, 1981, pp. 77–83.

"M200 Gas Chromatographs. Micro GC. Marco Performance.", MTI, 41762 Christy St., Fremont, CA 94538, 1989.

"Design of an Open–tubular Column Liquid Chromatograph Using Silicon Chip Technology", by A. Manz et al., *Sensors and Actuators*, B1 (1990), pp. 249–255.

(List continued on next page.)

*Primary Examiner*—Michael Brock

*Attorney, Agent, or Firm*—Westman, Champlin & Kelly, P.A.

[57] ABSTRACT

A gas chromatograph includes a manifold having a plurality of gas conduits formed therein. A valve module includes a support, a first valve mounted to the support and having a plurality of ports, and a column coupled to the support and being in communication with a port in the first valve. The valve module is pluggably engagable with the manifold. A detector is coupled relative to the column to detect gasses expelled from the column.

15 Claims, 10 Drawing Sheets

16 106 116 136 140 114 166 144 130 168 156 130 142 158 174 171 172 170

OTHER PUBLICATIONS

"Automatic Continuous Air Monitoring for Volatile Organic Compounds (VOCs)", CMS Research Corporation, Birmingham, Alabama, admitted prior art.

"The Series 2000 Minicams", CMS Research Corporation, Birmingham, Alabama, admitted Prior art.

"The Microsensor Technology, Inc. P200 Portable Micro Gas Analyzer", admitted prior art.

"Silicon Micromachining and High Speed Gas Chromatography", by Mark W. Bruns, Ph.D., *IEEE*, pp. 1640–1644, Sep. 11, 1992.

"SGC 3000 Smart Gas Chromatograph Applications Data", Aug. 1994, Honeywell.

OUTPUT CIRCUIT
20
ELECTRONICS MODULE
18
G.C. MODULE
16
TRANSMITTER MANIFOLD
14
GAS INPUT MODULE
12
CALIBRANT
SAMPLE
ACTUATOR PRESSURE
CARRIER GAS
10

3B
72
104
96
94
102
98
100
3B 72
104
94
102
96
98

16
116
72
74
126
58
60
A
B
A
B
126
126
114
112

16
106
110
108
58
126
60
110
78
64
122
62
124
120
116
114
138
134
128
136
144
132
118
140
130
132
140
130
142

16
106
136
116
114
140
144
156
158
168
130
142
174
172
171
170
166

MODULAR GAS CHROMATOGRAPH

This application is a continuation-in-part application of application Ser. No. 08/566,133, filed Dec. 1, 1995 now U.S. Pat. No. 5,808,179, entitled "MODULAR GAS CHROMATOGRAPH" and assigned to the same assignee as the present application. This application claims benefit of provisional application No. 60/004,618, filed Sep. 29, 1995.

INCORPORATION BY REFERENCE

The following U.S. patent application is hereby incorporated by reference:

U.S. patent Ser. No. 08/346,346, entitled IMPROVED MICROMACHINED VALVE ASSEMBLY and assigned to the same assignee as the present invention.

The following U.S. patent is hereby incorporated by reference:

U.S. Pat. No. 4,909,078 entitled FLUID FLOW DETECTOR, issued on Mar. 20, 1990 and assigned to the same assignee as the present application.

BACKGROUND OF THE INVENTION

The present invention deals with chromatography. More specifically, the present invention deals with a modular gas chromatograph formed as an easily replaceable module.

Gas chromatographs are used to measure various gas species in a gas sample. A portion of the gas sample is received at an inlet of the gas chromatograph. The gas sample is moved through a column which has an interior that is lined with one of any number of known materials, depending on the particular application or gas chromatograph being used. The column separates the larger and smaller molecules in the gas sample. Thus, the gas sample exits the column in such a manner that the first gas species out of the column is the one with the smallest and lightest molecules (a typical example is helium), while the last species is the one with the largest and heaviest molecules. The length of the column varies with each application. Typically, however, where there are a large number of species which the chromatographer desires to separate out from a single gas sample, the column must be quite lengthy.

The gas exiting the column is directed to a detector which detects the various gas species in the sample, as they exit the column. The detector, in turn, provides an output signal indicative of those gas species.

Conventional gas chromatographs include valves, detectors, piping, and heaters, all combined with various fittings, screws and connectors. These devices are all connected to one another in a manner which makes them difficult to repair and disassemble.

Further, different columns must be used for different applications. It is so difficult to change columns in present gas chromatographs, that this is very seldom done. Instead, different gas chromatographs are configured to test for different gas species or are configured to operate in different applications.

In addition, different types of chromatograph configurations require different valve configurations. For example, two known chromatograph configurations are a stripper configuration and a backflush configuration. These two require valves to be configured in a different manner. It is difficult to change valve configurations in conventional gas chromatographs.

SUMMARY OF THE INVENTION

A gas chromatograph includes a manifold having a plurality of gas conduits formed therein. A valve module includes a support, a first valve mounted to the support and having a plurality of ports, and a column coupled to the support and being in communication with a port in the valve. The valve module is pluggably engagable, as a unitary piece, with the manifold. A detector is coupled relative to the column to detect gasses expelled from the column.

DETAILED DESCRIPTION OF THE PREFERRED EMBODIMENTS

Figure 1:
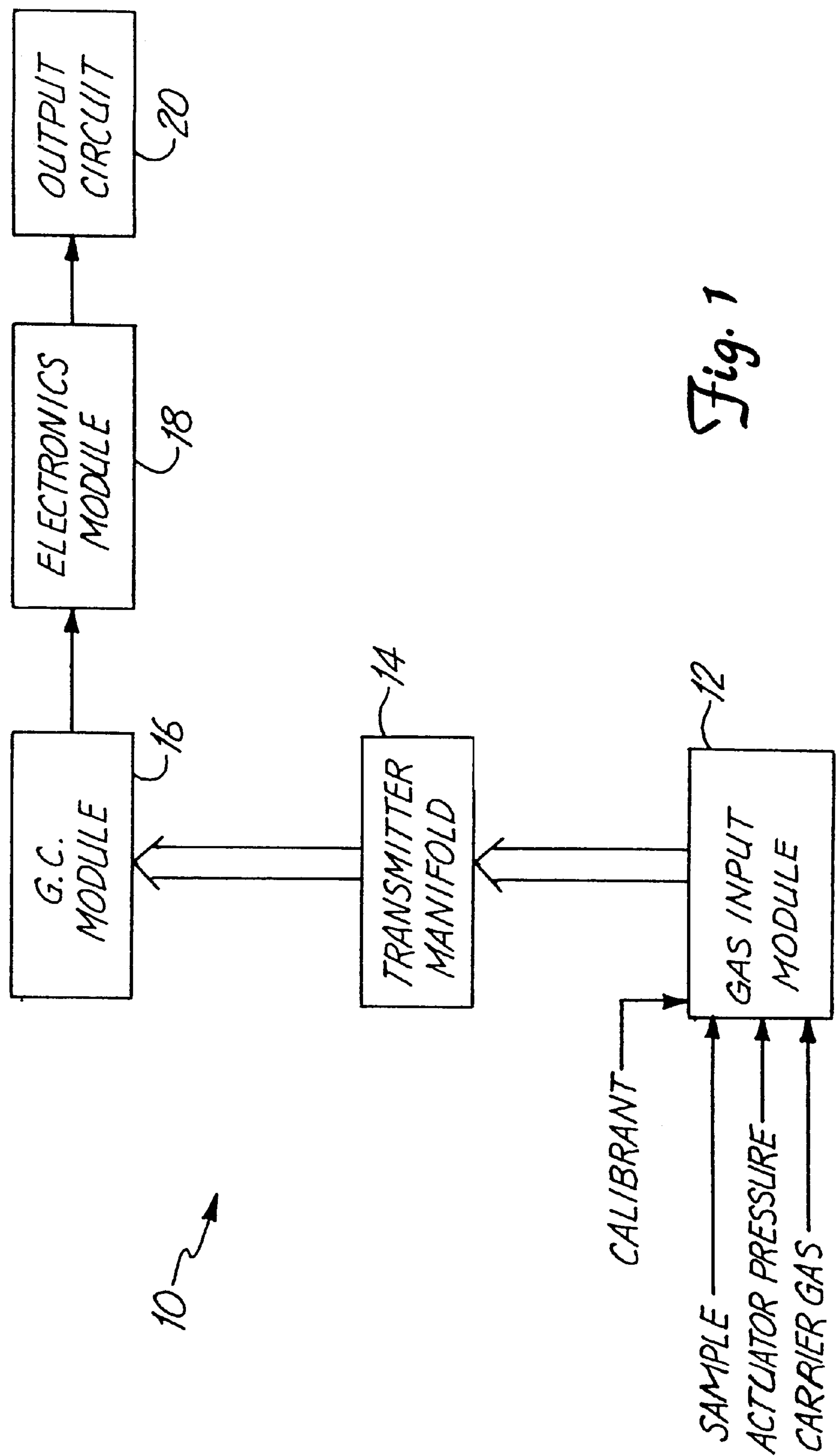
FIG. 1 is a block diagram of a gas chromatograph according to the present invention.

FIG. 1 is a block diagram of a gas chromatograph 10 according to the present invention. Gas chromatograph ("GC") 10 includes gas input module 12, transmitter manifold 14, GC module 16, electronics module 18 and output circuit 20.

Gas input module 12 receives a calibration gas, the gas sample to be analyzed, an input from an actuator pressure source, and a carrier gas. In one preferred embodiment, the carrier gas also acts as the actuator pressure source. The gas input module 12 receives these inputs and provides either the gas sample or a calibration gas, along with a regulated carrier gas, to the transmitter manifold 14.

The transmitter manifold 14 includes a variety of solenoids and corresponding valves (solenoid valves) which are operated as pilots to control valves which, in turn, control input of either the sample or calibrant. The solenoid valves also provide pilot signals (valve manipulation signals) to the GC module 16. The transmitter manifold 14 transmits both the valve actuation signals, as well as either the calibrant or sample gas, and also the carrier gas, to GC module 16.

GC module 16 receives these inputs and passes the sample gas through a desired valve configuration. The output from the valve configuration is provided to a detector, such as a mass spectrometer, thermal conductivity detector, or other detector whose output is indicative of the various gas species and/or specie concentration in the sample. Typically, the specie is indicated by the elution time and the concentration is indicated by the area under the output signal.

The detector output is provided, preferably as an analog signal, to electronics module 18. Electronics module 18 conditions the analog signal by providing amplification, filtering, linearization, and other required signal conditioning, and provides the conditioned analog signal to output circuit 20. In the preferred embodiment, output circuit 20 is a chart recorder or monitoring computer or other suitable output transmission circuit which provides an output signal indicative of the gas species and species concentration detected.

Figure 2A:
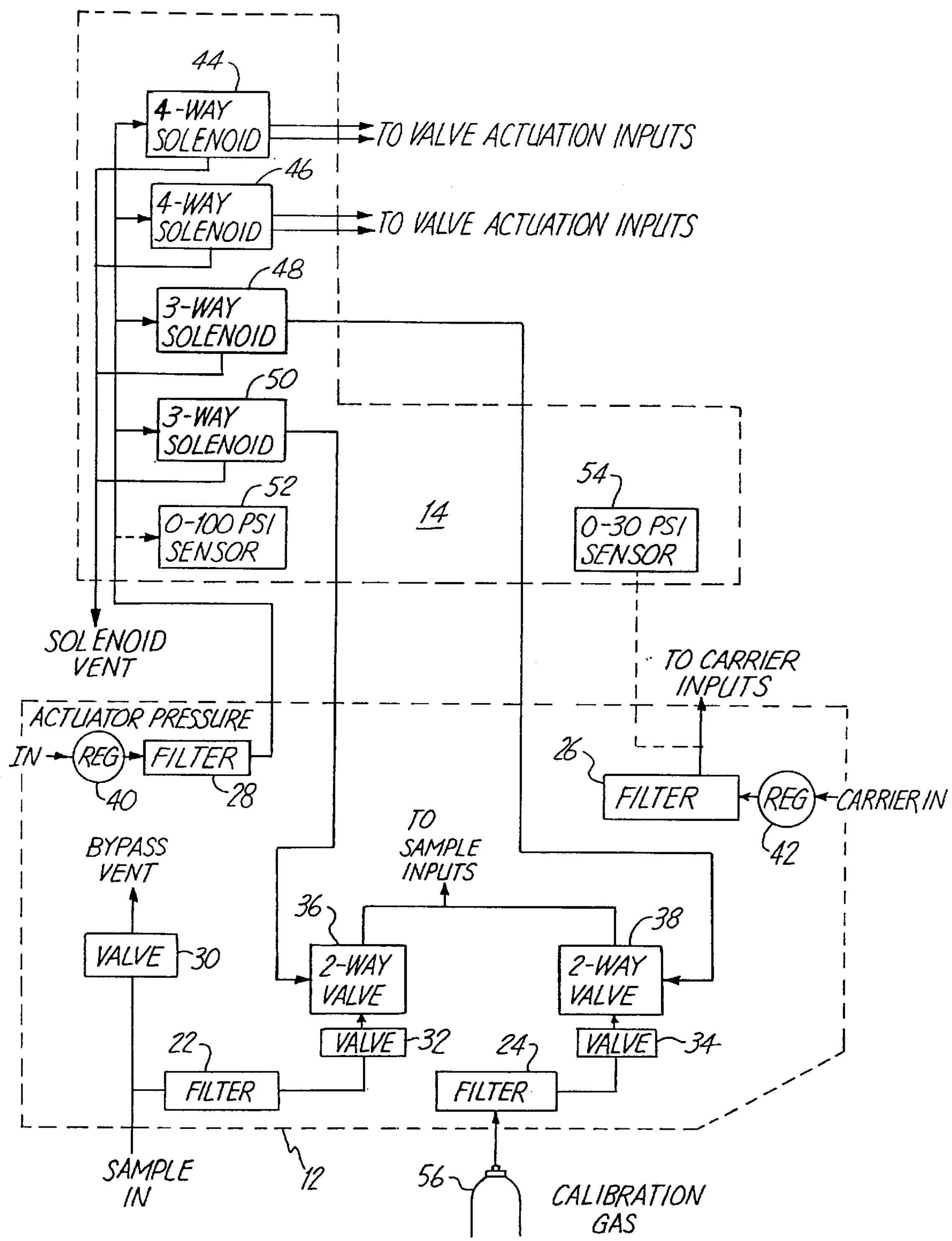
FIGS. 2A and 2B are more detailed block diagrams illustrating the gas chromatograph shown in FIG. 1.
Figure 2B:
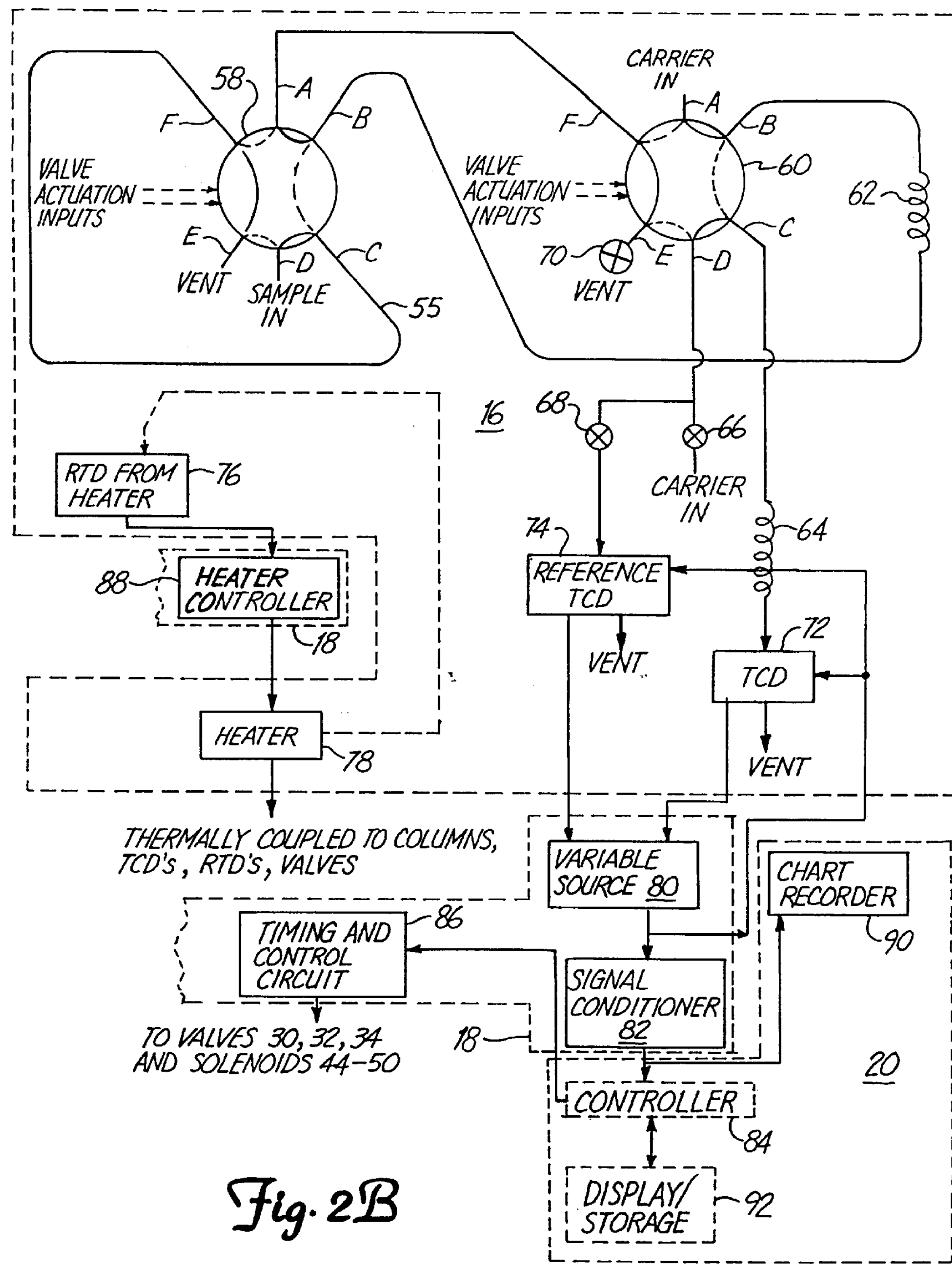

FIGS. 2A and 2B illustrate, in greater detail, the gas chromatograph system 10 shown in FIG. 1. FIGS. 2A and 2B are in partial block diagram and partial schematic form. FIG. 2A illustrates gas input module 12 and transmitter manifold 14, while FIG. 2B illustrates GC module 16, electronics module 18 and output circuit module 20.

Gas input module 12 includes filters 22, 24, 26 and 28, flow restrictors 30, 32 and 34, two-way valves 36 and 38 and pressure regulators 40 and 42 arranged as shown. Transmitter manifold 14 includes two four-way solenoid valves 44 and 46, three-way solenoid valves 48 and 50 and a pair of pressure sensors 52 and 54. The sample gas is input from the sample under analysis through filter 22 and valve 30. Valve 30 is preferably a needle valve which acts as a restrictor. When the sample is desired to be analyzed, the sample is provided through filter 22.

Filter 22 is preferably a 0.5 micron filter which filters the gas sample input to the gas chromatograph 10. The filtered gas flow is provided to two-way valve 36 through a valve 32. As with valve 30, valve 32 is preferably a flow restrictor which acts to even out pressure fluctuations (or flow changes) in the tubes providing the sample to gas chromatograph 10.

Actuator pressure is applied at an input to regulator 40. The regulated actuator pressure is then applied to filter 28 which is also a 0.5 micron filter which serves to filter the actuator pressure input. The regulated and filtered actuator input is then provided to sensor 52 and to solenoids 44, 46, 48 and 50.

Sensor 52, in a preferred embodiment, is a pressure sensor which senses pressure in a range of 0 to 100 pounds per square inch (psi). Sensor 52 either provides an output which is coupled to a visually observable gauge, or it can provide an electronic output coupled to a controller which is suitable for shutting down power to the system if the pressure is outside a desired range. All of solenoid valves 44, 46, 48 and 50 (solenoid valves 44–50) are electronically controlled solenoid valves which receive the actuator pressure at inputs thereof, and provide it at one or more of the outputs thereof. Solenoid valves 44–50 all have an output which is provided to a solenoid vent. Further, three-way solenoid valve 50 has an output which is coupled to two-way valve 36. Therefore, when solenoid valve 50 is operated to provide the actuator pressure at the output connected to two-way valve 36, two-way valve 36 is configured to pass the filtered sample from its input to its output. The output of valve 36 is connected to GC module 16 (discussed in greater detail with respect to FIG. 2B).

Gas input module 12 is also configurable to provide a calibration gas to GC module 16. A calibration gas bottle 56 contains calibration gas and provides it under pressure to filter 24. As with filter 22, filter 24 is a 0.5 micron filter which acts to filter the calibration gas. The filtered gas flow is output to valve 34 which acts as a flow restrictor and provides the calibration gas to two-way valve 38.

As with two-way valve 36, valve 38 is a pneumatically controlled valve which has an input receiving the calibration gas from valve 34, and an output coupled to GC module 16. Two-way valve 38 also has an actuator input which is coupled to the output from three-way solenoid 48. Valves 36 and 38 are preferably operated in a manner to provide "atmospheric standardization" of the gas sample. This type of operation is also known as block and bleed operation. This is accomplished by venting the sample input tube 55 (described in greater detail with respect to FIG. 2B) to atmospheric pressure after it has been filled with the gas to be measured. Thus, valve 36 is opened to allow the gas sample to flow to GC module 16 into the sample tube 55 and out the vent port. Just prior to switching valve 58 to connect sample tube 55 to the carrier gas, solenoid 50 is controlled to close valve 36. Tube 55 is still connected to the vent port and allowed to bleed to atmospheric pressure. Valve 58 is then controlled to connect sample tube 55 to the carrier gas, as is described in greater detail with respect to FIG. 2B.

To calibrate the gas chromatograph system 10, valves 36 and 38 are also operated in block and bleed fashion. Three-way solenoid valve 50 is first configured to remove the actuator pressure from the actuator input to two-way valve 36. Three-way solenoid valve 48 is then configured to provide the actuator pressure to the actuator input of two-way valve 38. This operation closes both valves 36 and 38 for a short period and then opens two-way valve 38 so that the calibration gas, rather than the sample gas, flows to GC module 16.

Four-way solenoid valves 44 and 46 receive actuator pressure from filter 28 at inputs thereof, and are controllable to provide the actuator pressure at two of four outputs. In one configuration, four-way solenoid valves 44 and 46 provide the actuator pressure to the solenoid vent output which vents the actuator pressure. In another configuration, four-way solenoid valves 44 and 46 provide the actuator pressure to valves 58 and 60 in the GC module 16 discussed in greater detail with respect to FIG. 2B. The outputs from four-way solenoid valves 44 and 46 which connect to valves 58 and 60 are preferably dual valve actuation outputs for actuating the valves 58 and 60.

In addition, a carrier gas is provided to gas input module 12 through regulator 42. The carrier gas is regulated to a desired pressure and is also provided to filter 26. Filter 26 is a 0.2 micron filter which acts to filter the carrier gas input. The output from filter 26 connects to valves in GC module 16. Further, pressure sensor 54, located in transmitter manifold 14, couples to the output of filter 26 to sense the pressure of the carrier gas. Pressure sensor 54 is preferably a 0–30 psi pressure sensor. As with sensor 52, sensor 54 provides an output which can be used to control regulator 42 based on a determination of whether the carrier gas is within a desired pressure range, or simply to display the pressure. In one preferred embodiment, the carrier gas is provided by the same source as the gas which provides the actuator pressure. In that case, regulators 40 and 42 are used to regulate the gas input to obtain desired pressures for the actuator pressure and the carrier gas input.

FIG. 2B illustrates a more detailed block diagram of gas chromatograph module 16, electronics module 18 and output circuit module 20. Gas chromatograph module 16 includes, in the embodiment shown in FIG. 2B, two multi-position, multi-port valves 58 and 60. Gas chromatograph module 16 also includes first column 62 and second column 64, needle valves 66, 68 and 70, thermal conductivity detector 72, reference thermal conductivity detector 74, resistive temperature detector 76 and heater 78. Electronics module 18 includes programmable power supply 80, signal conditioner 82, timing and control circuit 86 and heater controller 88. Output circuit module 20 includes chart recorder 90 and optional controller 84 and display/storage circuit 92.

Valves 58 and 60 are preferably micromachined valves formed according to the specification in U.S. patent application Ser. No. 08/346,346 assigned to the same assignee as the present invention, and hereby incorporated by reference. Briefly, the valves are formed by a brittle layer of material having a number of ports opening therein, and valve seats formed about perimeters of the ports. The valve seats are selectively covered to control fluid flow through the ports. A flexible sheet of material is secured to the brittle layer of material to form a diaphragm which is actuated through a control force provided at the valve actuation inputs from solenoid valves 44 and 46 in transmitter manifold 14. Under the control force, the diaphragm is controlled to selectively cover the valve seats and control fluid flow through the ports.

In the preferred embodiment shown in FIG. 2B, valves 58 and 60 each have six ports labeled A–F. Also, in the preferred embodiment, valves 58 and 60 are configurable in one of two states based on the valve actuation inputs. In a first state, the ports are connected as shown by the solid lines. When the valve actuation inputs are changed (i.e., to a second state), the ports are connected as shown by the dashed lines. It should be noted that, in the preferred embodiment shown in FIG. 2B, valves 58 and 60 are coupled in a single column stripper configuration. Other configurations are also contemplated.

In operation, calibration gas can initially be provided to valve 58 instead of a sample. The calibration procedure permits timing characteristics of GC 10 to be calculated, which timing characteristics are used in later determination of gas species in the sample gas. The calibration gas also provides a concentration reference.

In the stripper configuration, valves 58 and 60 are placed in the first state so that the ports are connected as shown by the solid lines. In this state, the sample gas input at port D of valve 58 runs into port D, out through port C, in through port F and out through port E (where it is vented), all in valve 58. This step fills tube 55 connecting ports C and F with a known volume of sample gas.

Also, in this state, carrier gas is input at port A of valve 60, output at port B, runs through column 62, is input at port B of valve 58, output through port A of valve 58, input at port F of valve 60 and output at port E of valve 60 (where it is vented). Further, carrier gas is input, through needle valves 66 and 68, at port D of valve 60, output through port C, provided through column 64 and output (through thermal conductivity detector 72) to vent. Valves 58 and 60 are maintained in this state for at least a predetermined duration. With the carrier gas running through columns 62 and 64, reference thermal conductivity detector 74 provides an output which is indicative of a baseline condition.

Then, the valve actuation inputs to valves 58 and 60 are manipulated (according to a block and bleed operation) so that valves 58 and 60 simultaneously switch to the second state, in which the ports are connected as shown by the dashed lines. In this state, the sample gas input at port D of valve 58 is simply output to vent through port E. In addition, the carrier gas input through port A of valve 60 is connected through port A of valve 58 and output through port F of valve 58. Thus, the carrier gas pushes the sample gas previously accumulated in the tube 55 connecting ports C and F of valve 58, in through port C and out through port B of valve 58, through first column 62, in port B of valve 60 and out port C of valve 60 where it is passed through column 64. Once the sample gas is output from column 64, it is provided to, in the preferred embodiment, thermal conductivity detector 72. Thermal conductivity detector 72 is described in greater detail with respect to FIG. 3A. Essentially, thermal conductivity detector 72 is operated to detect the thermal conductivity properties of the gas species impinging thereon. In this way, thermal conductivity detector 72 provides an output indicative of the concentration of the gas species impinging thereon.

Reference thermal conductivity detector 74 is coupled to receive the carrier gas and provide it to vent. Thus, reference thermal conductivity detector 74 provides a reference signal which is used by signal conditioner 82 in combination with the output from thermal conductivity detector 72 to more accurately detect the gas species of interest. This is described in greater detail with respect to FIG. 2C.

Referring again to FIG. 2B, thermal conductivity detectors (TCDs) 72 and 74 are highly sensitive to pressure fluctuations in the conduits conducting the gas flow. Therefore, needle valves 66, 68 and 70 are provided and are dimensioned to approximate, or simulate, columns 62 and 64. In other words, it can be seen that, during normal operation of valves 58 and 60, the sample and carrier gases are alternately provided through columns 62 and 64, and to vent. Columns 62 and 64 have a relatively small diameter, and a relatively long length. Therefore, unless there is some flow restriction in the vent channel, flow changes and thus pressure fluctuations are developed in the conduits as gas flow is redirected by switching of valves 58, 60. By providing needle valves 66, 68 and 70, additional columns are simulated in the vent channel. This has the effect of evening out, or substantially eliminating, pressure fluctuations caused by switching actuation of valves 58 and 60. This is particularly important because, in gas chromatography, the more species of gas which are desired to be separated out of a gas sample, the longer the columns required. Exceedingly long columns exacerbate the problem of pressure fluctuations. Therefore, by providing needle valves 66, 68 and 70, longer columns can be used in the gas chromatograph 10. Needle valves 66, 68 and 70 are also preferably adjustable to change the width and the spacing of the output peaks indicative of the various species exiting column 64.

TCDs 72 and 74, and columns 62 and 64, are sensitive to changes in ambient temperature. Therefore, heater 78 is disposed on gas chromatograph module 16 and is in thermal contact with columns 62 and 64, TCDs 72 and 74, RTD 76 and valves 58 and 60. All of these things being in thermal contact provides uniform heating of module 16 which improves performance. Resistive temperature detector (RTD) 76 is disposed on heater 78 and relatively closely proximate TCD 72. RTD 76 is an element which has a resistance that changes with temperature. RTD 76 thus provides an output indicative of the temperature of heater 78 and TCD 72. This output is provided to heater controller 88 which is mounted in electronics module 18 and which provides an output that controls heater 78. This closed loop control maintains module 16 at an elevated, stable temperature.

The outputs from reference TCD 74 and TCD 72 are provided to a programmable power supply 80 in electronics module 18. In a preferred embodiment, TCD 72 is operated in a constant temperature mode. In other words, a voltage is applied to TCD 72 to induce a current running therethrough that heats TCD 72 to a desired temperature. As the gas impinging on TCD 72 dissipates heat generated by TCD 72, the voltage applied to TCD 72 is changed to maintain TCD 72 at a desired temperature. The signal indicative of the voltage applied to TCD 72 is thus indicative of the thermal conductivity properties of the gas species then impinging on TCD 72.

TCD 72 therefore output a signal indicative of the temperature of TCD 72 to variable source 80. Based on this temperature signal, variable source 80 provides an output signal to either increase, decrease, or maintain, the voltage applied across TCD 72. This signal is provided to signal conditioner 82 where it is preferably conditioned (such as amplified, filtered, etc.).

Figure 2C:
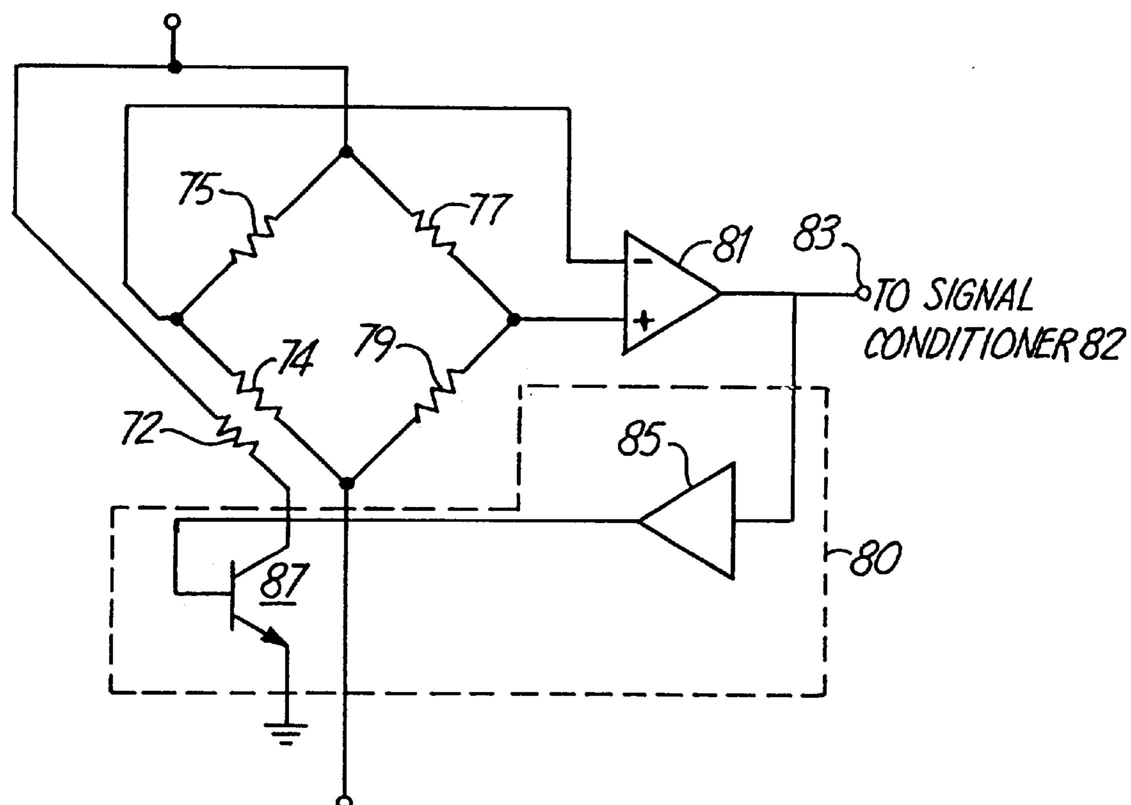
FIG. 2C illustrates one embodiment of a specific implementation of the thermal conductivity detectors.

FIG. 2C shows one embodiment of the implementation of a sensing and control system with TCDs 72 and 74 in a standard Wheatstone bridge configuration. Reference TCD 74 is included in a bridge circuit to be provided between positive and negative voltage supplies at the small, open circle terminals shown. This bridge circuit has therein further resistors 75, 77 and 79 which are provided at a stable temperature as reference resistance values.

Thus, if the temperature of TCD 72 should change because, for instance, of an increase in gas flow thereby, there will be a corresponding change in the temperature and electrical resistance of reference TCD 74. This change in resistance will lead to a change in the voltage across the bridge between the two inputs of a differential averaging means 81. Differential averaging means 81 will provide a signal at its output 83, which is an average of the signal developed across the bridge containing reference TCD 74 and resistors 75 through 79.

This same output signal will be used to drive signal conditioner 82 and a feedback loop including a buffer means 86 which in turn drives the base of an npn bipolar transistor 87, both of which form the variable source 80. Thus, the signal at output 83 is used to control the amount of current transistor 47 permits to be drawn through TCD 72 to thereby control its temperature. Hence, in the feedback system of FIG. 2C, changes in temperature occurring in TCD 72 because of varying fluid flow conditions are counteracted by the action in the feedback loop of FIG. 2C to maintain TCD 72 at a preselected temperature. The average signal required to do this is present at system output 83 and therefor its value is a measure of the heat transfer effect of the flowing gas on TCD 72.

The analog signal from output 83, after it is conditioned, is also preferably provided to chart recorder 90 in output circuit 20 where it is recorded for later observation. An optional controller 84 (such as a digital computer) is also provided in electronics module 18. Controller 84 is preferably provided with the capabilities of linearizing and digitizing the analog signal provided by signal conditioner 82 to provide a digital signal indicative of the gas species then impinging on TCD 72. This digital signal can be communicated, or transmitted, to display/storage circuit 92 which preferably includes an operator-observable display and memory for storing desired information output from controller 84. In addition, controller 84 preferably provides an output to timing and control circuit 86 to accommodate desired timing and actuation of valves 30, 32 and 34 and solenoid valves 44–50.

In the preferred embodiment, all of the vented gas is plumbed together and provided to a scrubbing system and then vented to atmosphere.

Figures 3A, 3B:
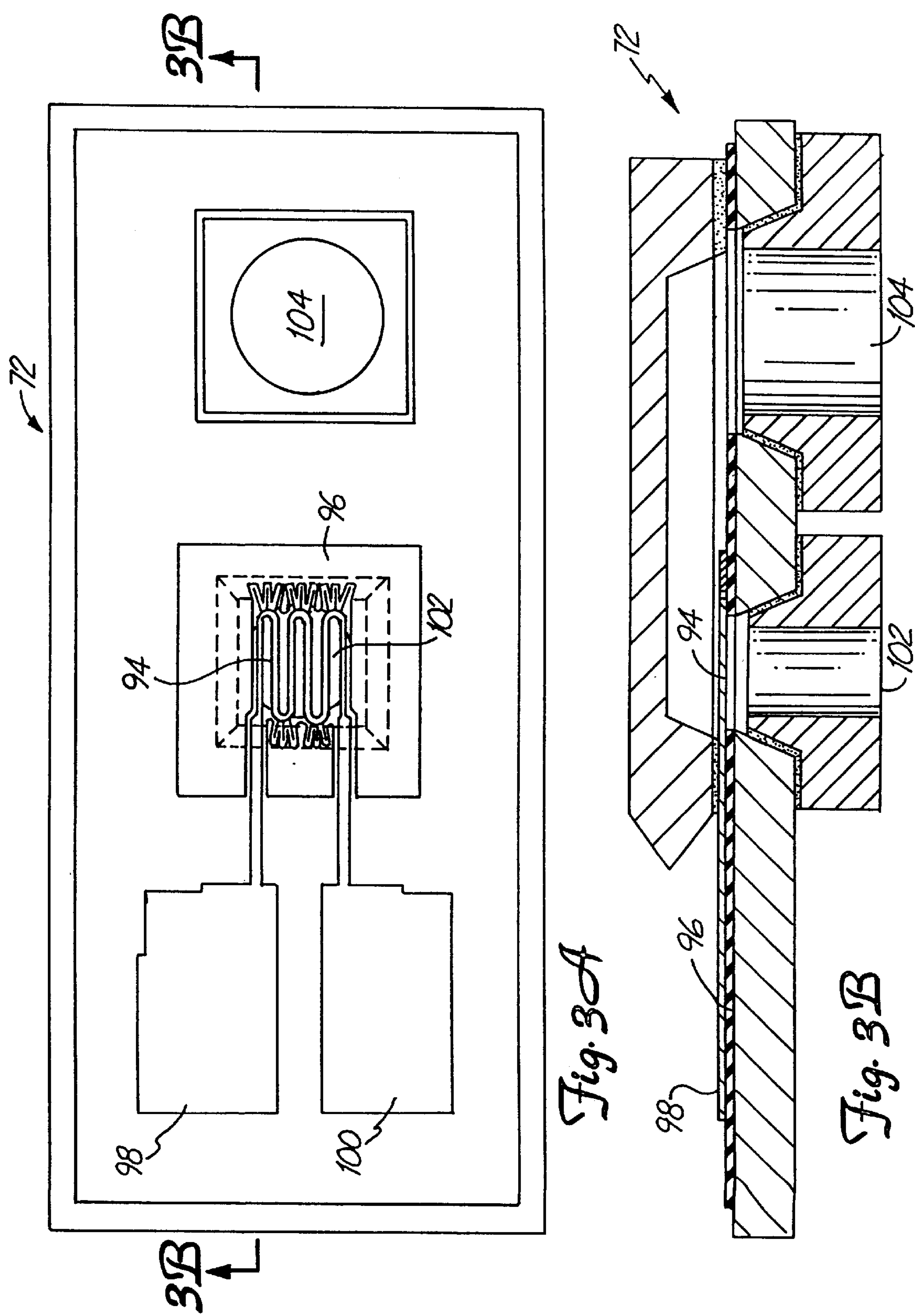
FIGS. 3A and 3B illustrate one embodiment of a thermal conductivity detector according to the present invention.

FIGS. 3A and 3B illustrate a thermal conductivity detector (TCD) used in system 10 (such as TCD 72 or 74). Such detectors are described in greater detail in U.S. Pat. No. 4,909,078 which is hereby incorporated by reference. Briefly, TCD 72 includes a bridge member 94 suspended over an orifice plate 96. A plurality of contacts 98 and 100 are coupled to bridge 94. Contacts 98 and 100 are used both to apply a voltage to member 94, and to measure resistance of member 94 to monitor the temperature of member 94. In operation, gas enters through passageway 102, impinges upon and flows across member 94 and exits through passageway 104. A varying amount of voltage is applied across pads 98 and 100 to keep member 94 at a substantially constant temperature. Based on the value of the voltage applied across pads 98 and 100, the thermal conductivity characteristics of the gas then impinging on member 94 is determined and the particular gas concentration is, in turn, determined using well known methods. The gas species is identified by the timing of the output signal as it correlates to the calibration gas.

Figure 4B:
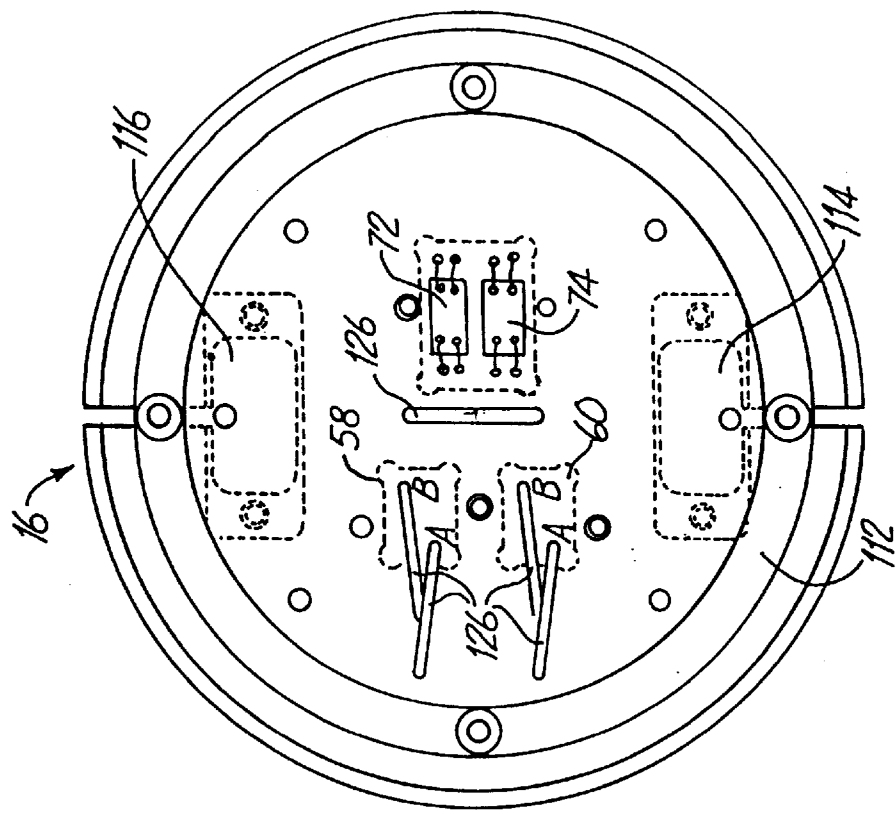
FIGS. 4A and 4B illustrate a valve module according to the present invention.
Figure 4A:
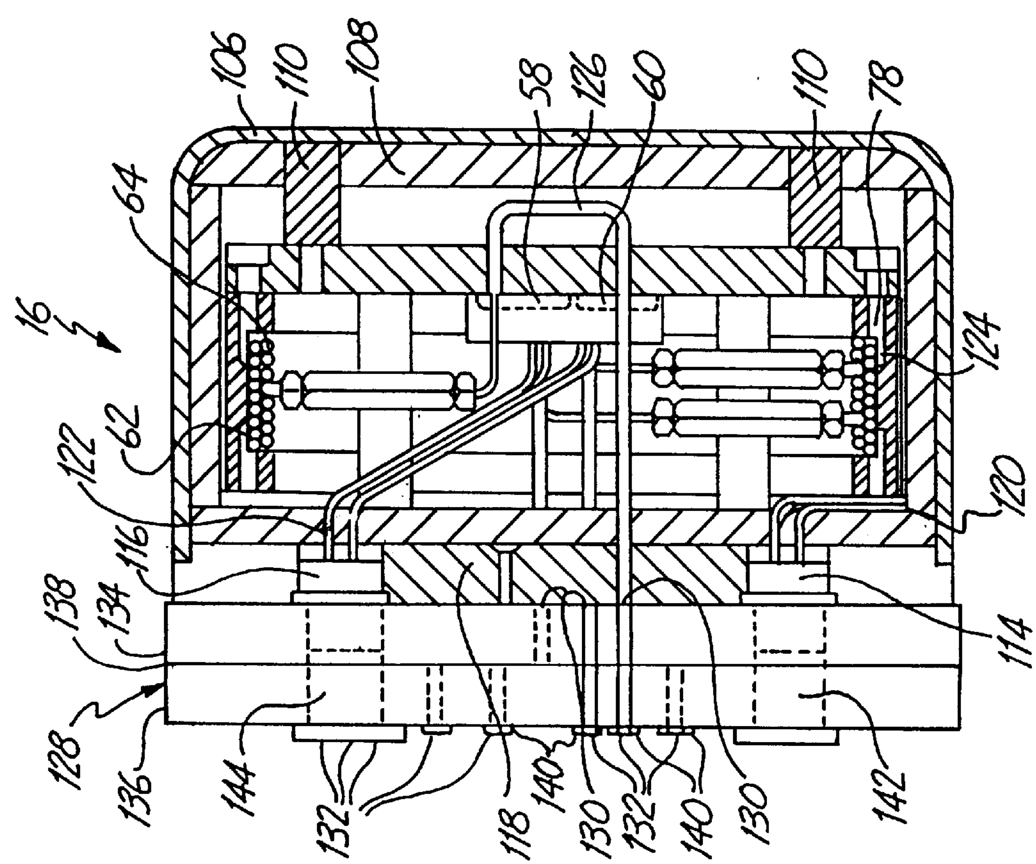

FIGS. 4A and 4B better illustrate GC module 16. FIG. 4A is a cross-sectional view of module 16 while FIG. 4B is a top view with the top cover of module 16 removed. Module 16 includes the items schematically designated in FIG. 2B, and those items are similarly numbered in FIGS. 4A and 4B. In addition, module 16 includes a cap 106 which houses a lining of thermal insulation 108. Insulation 108 is coupled, by thermally insulating stand-off material 110, to spool heater 78. Spool heater 78 is preferably a metal foil heater on polyimide.

A pair of electrical connectors 114 and 116 are also coupled within cap 106, and to thermally insulating stand-off material 118. Electrical connector 114 has a plurality of conductors 120 coupled to spool heater 78. Electrical connector 116 has a plurality of conductors 122 which are coupled to TCDs 72 and 74. Spool 78 is formed substantially as an annular ring with a grooved interior surface 124. Columns 62 and 64 are formed of resilient metal tubing (such as stainless steel) or fused silica which is spring loaded against grooved surface 124, and which exerts radial outwardly directed force against surface 124. This holds columns 62 and 64 in place within spool 78.

Module 16 also includes a pluggable manifold 128 formed of a plurality of layers including plates 134 and 136 and separation layer 138. Plates 134 and 136 have major surfaces which sandwich layer 138. Apertures 130 and 132 are provided in plates 134 and 136 and communicate with corresponding passageways formed (preferably by drilling) in plates 134 and 136. The passageways provide the necessary piping between apertures 130 and 132 to conduct gas through plates 134 and 136 to and from the remainder of module 16. The separation layer 138 provides the necessary routing in a plane generally defined by the major surfaces of plates 134 and 136 to achieve desired plumbing. The separation layer 138 is described in greater detail with respect to FIG. 5.

It should be noted that apertures 130 define openings which may conduct gas into module 16 or out of module 16. The same is true for apertures 132. However, for the sake of simplicity, the apertures designated by numeral 130 will be referred to as inputs and those defined by numeral 132 will be referred to as outputs.

The outputs 132 include tubes extending out of plate 136 in manifold 128. Those tubes have gaskets or o-rings 140 disposed therearound. This provides for a better sealing pluggable connection into a mating baseplate. This connection will be described in greater detail with respect to FIGS. 6A and 6B.

Also, manifold 128 has apertures for receiving mating connectors 142 and 144. Mating connectors 142 and 144 pluggably mate with connectors 114 and 116, respectively. Connectors 142 and 144 provide a plurality of conductors carrying the desired electrical signals.

Figure 5:
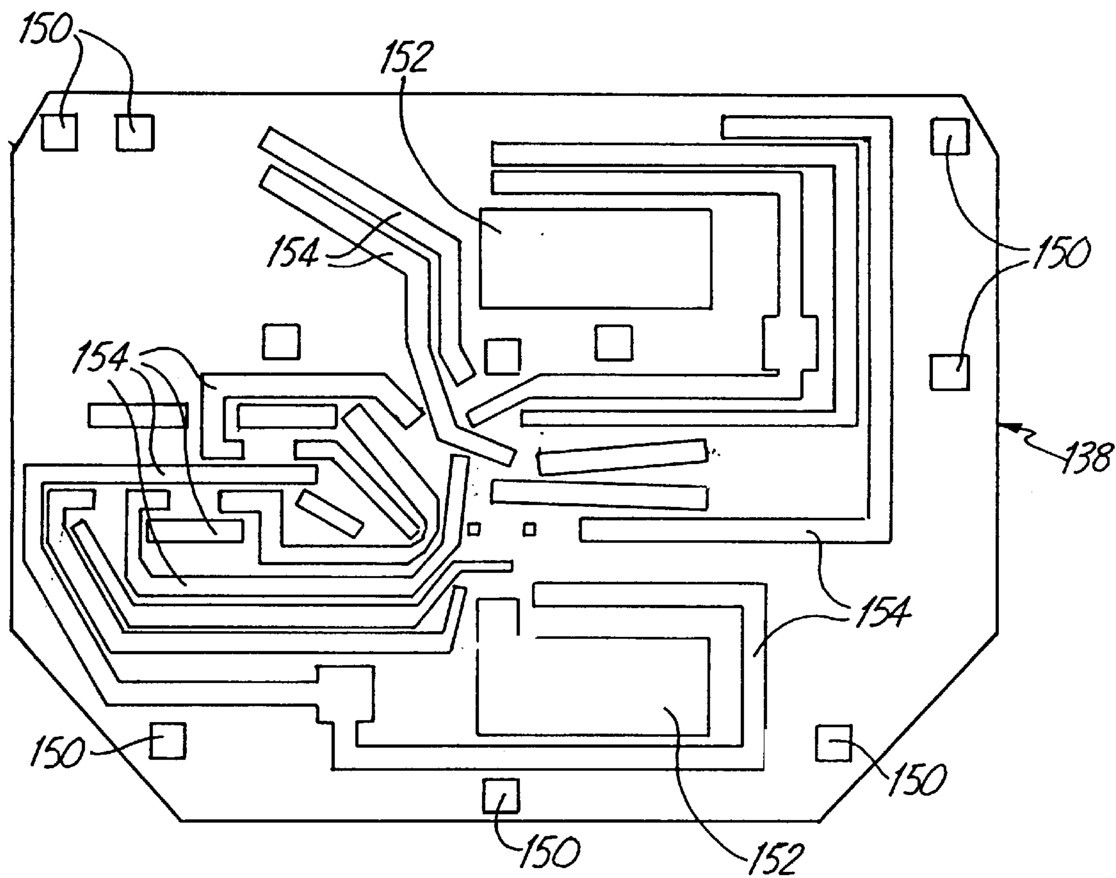
FIG. 5 illustrates a manifold separation layer according to the present invention.

FIG. 5 is one illustration of a preferred embodiment of separation layer 138 of manifold 128. Separation layer 138, in the preferred embodiment, is simply a gasket formed of any suitable material, such as polyimide laminated with teflon which provides a hermetic seal between plates 134 and 136. Layer 138 has a plurality of voids formed therein. In the embodiment shown in FIG. 5, a plurality of voids 150 are provided for securing means, such as screws, clips or pins to fit therethrough. In addition, voids 152 are provided for electrical connectors 142 and 144. Voids 154 are provided to define the channeling necessary to channel gases and pressure from inlets 130 to outlets 132 (and vice versa) in manifold 128.

It should also be noted that, in the preferred embodiment, the gas sample under analysis which passes through manifold 128 passes directly or straight through from plate 134 to plate 136 in a linear fashion, and does not run any significant distance in the plane generally defined by gasket 138. Therefore, gaseous contact between the gas sample and gasket 138 is minimized. Since the gasket 138 is preferably an organic material, it may introduce contaminants such as carryover from a previous gas sample which would tend to influence the results of the chromatographic analysis. By limiting the exposure of the gas under analysis to the gasket, this problem is significantly reduced or eliminated. This arrangement also reduces time required to flush the system between samples because dead volume is kept to a minimum. Further, this arrangement reduces discontinuously contoured interior surfaces, such as sharp turns, which also require long flush intervals.

Figure 6A:
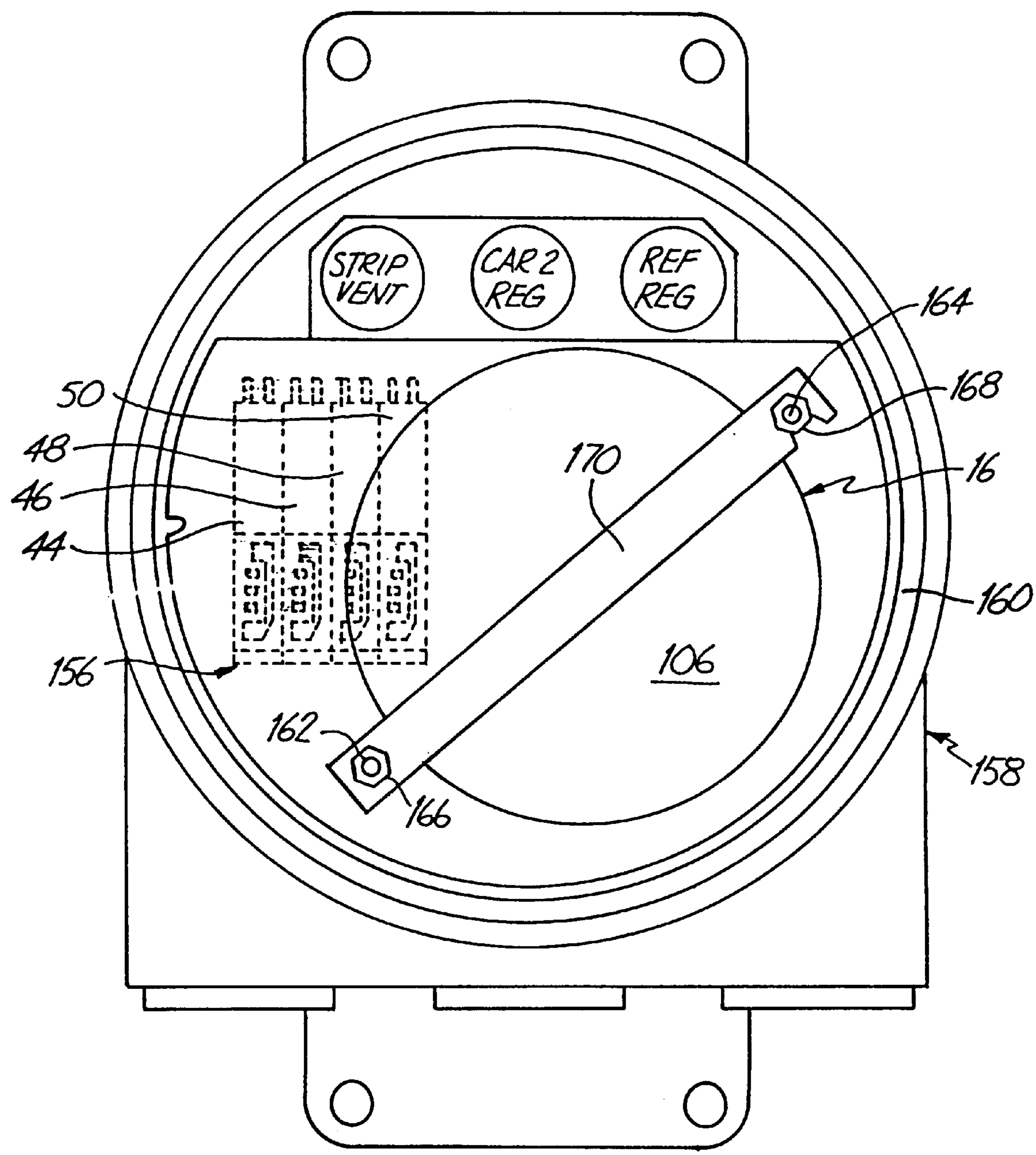
FIGS. 6A and 6B illustrate the pluggable nature of the gas chromatograph according to the present invention.
Figure 6B:
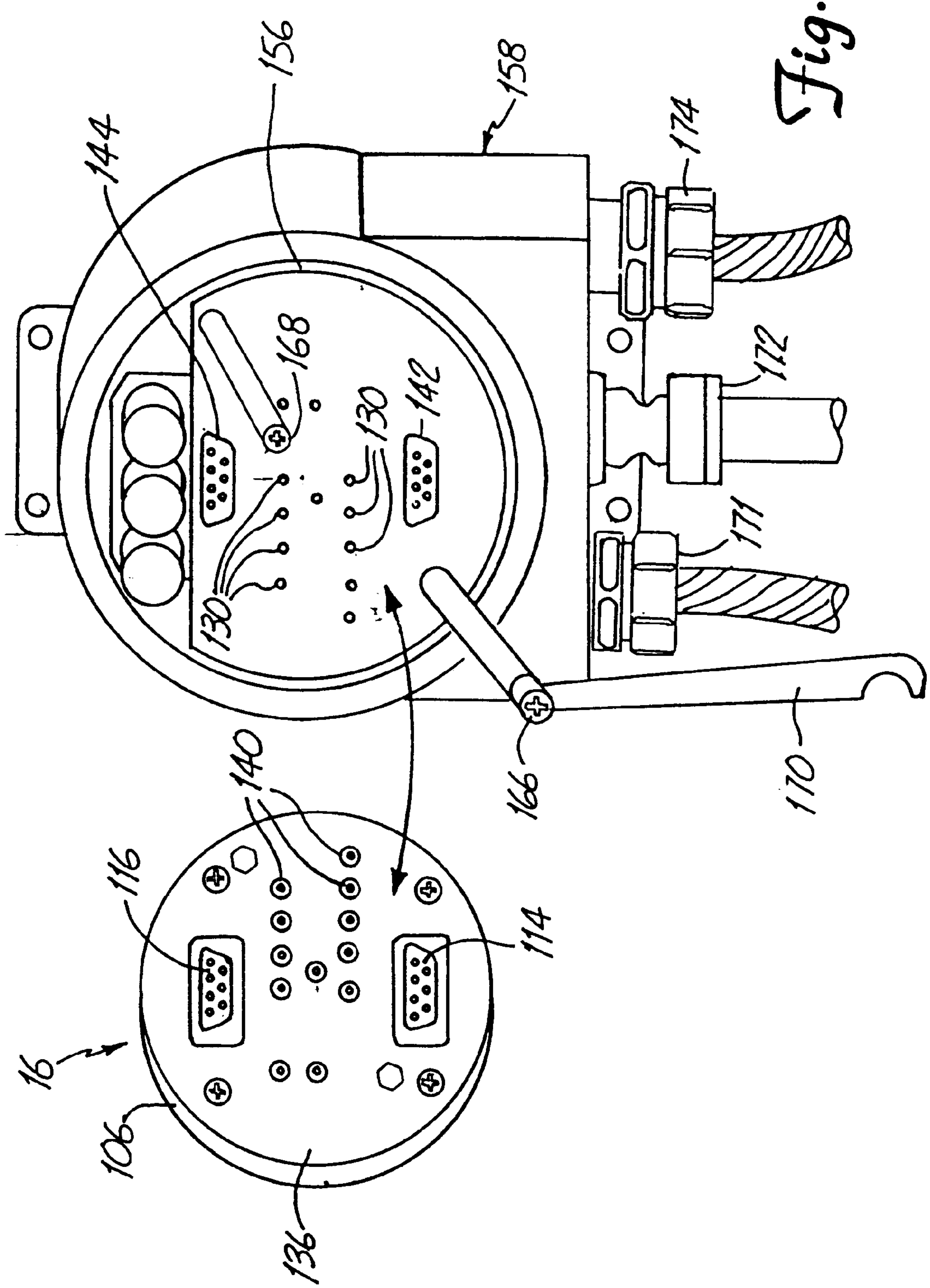

FIG. 6A better illustrates a preferred physical configuration of GC module 16. FIGS. 6A and 6B illustrate a number of the same items previously described, and those items are similarly numbered. FIG. GA is a front view of module 16 pluggably engaged in a baseplate 156 inside housing 158. Housing 158 normally has a threaded cover threadably engaging threads 160 to enclose transmitter module 16. However, for the sake of clarity, the cover is shown removed from FIG. GA. Solenoids 44, 46, 48 and 50 are shown in phantom in FIG. 6A.

Module 16 is pluggably engageable into baseplate 156. This is shown more clearly in FIG. 6B. However, FIG. 6A shows the means by which module 16 (including cap 106) are secured to baseplate 156.

A plurality of stand-offs which threadably engage baseplate 156 project outwardly from baseplate 156 and terminate in threadable ends 162 and 164. Nuts 166 and 168 are threadably secured to ends 162 and 164, respectively. Locking bar 170 extends between the two stand-offs to secure cap 106 (and module 16) to baseplate 156. Nuts 166 and 168 are tightened on threaded ends 162 and 164 so that locking bar 170 exerts a securing force against cap 106 to keep module 16 in place, pluggably engaged with baseplate 156.

FIG. 6B shows system 10 with module 16 unplugged from baseplate 156. In order to unplug module 16, one simply loosens nuts 166 and 168 and rotates clamping bar 170 so that it no longer covers cap 106. Module 16 can then by unplugged by hand since it is preferably only held in place by the plugging friction of electrical connectors 114 and 116 mating with connectors 142 and 144.

In a preferred embodiment, housing 158 is also provided with threadable bosses 171, 172 and 174. The electrical conductors from connectors 142 and 144 exit through bosses 171 and 174, and through appropriate conduits. The tubes which conduct the gas and air pressure among gas input module 12, transmitter manifold 14 and gas chromatograph module 16 pass through boss 172 and an appropriate pipe or other conduit.

Figure 7:
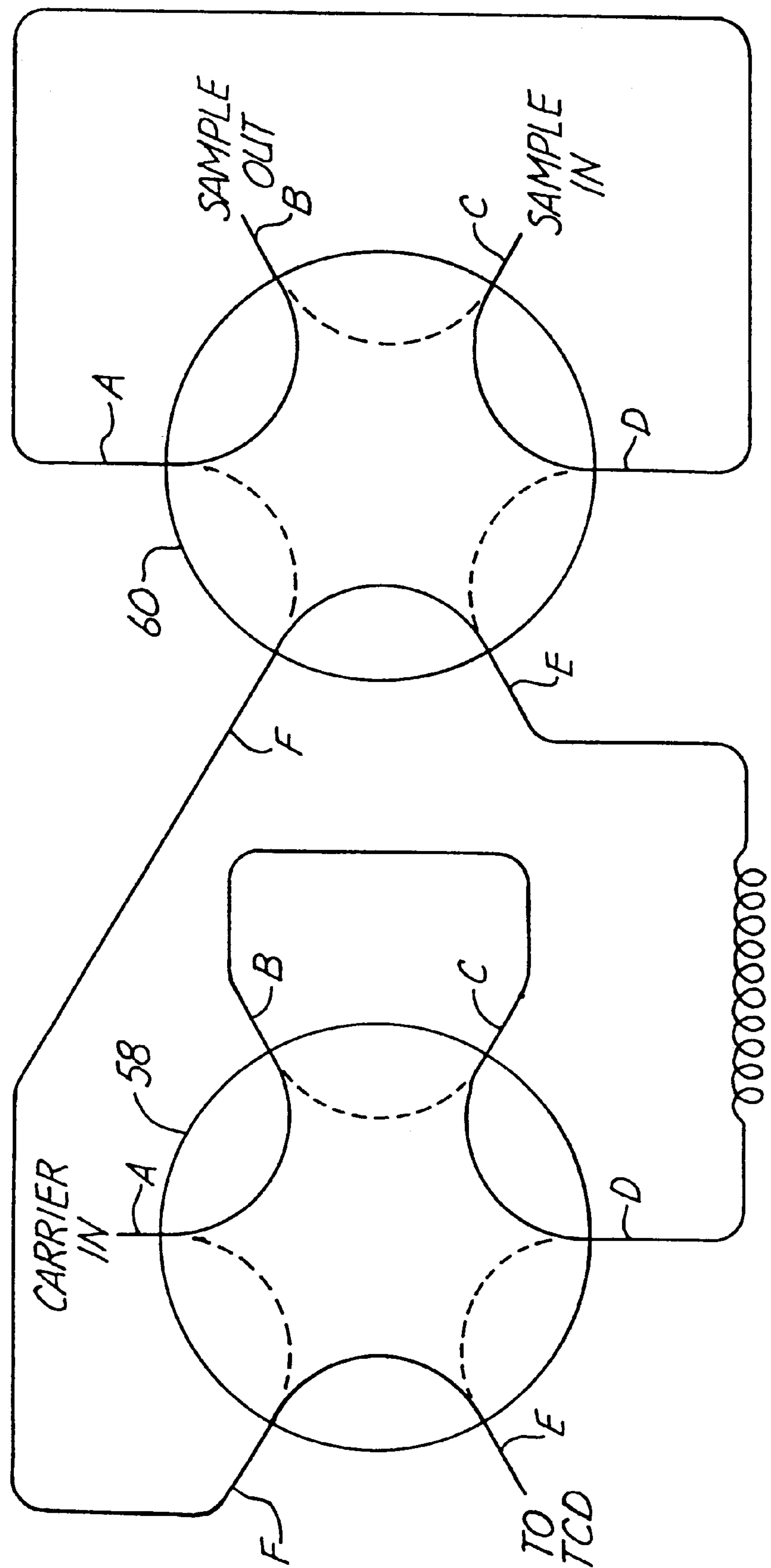
FIG. 7 illustrates a second valve configuration in which the valves are connected in a backflush configuration.

FIG. 7 simply shows another embodiment of a chromatograph configuration according to the present invention. In FIG. 7, valves 58 and 60 are connected in a single column backflush configuration. This type of configuration can easily be integrated into a module 16 according to the present invention. Further, a single valve can also be used, and a single, single-position valve can be utilized, depending on the desired column configuration.

Thus, the present invention provides a gas chromatograph module 16 which is pluggably removable from a remainder of the system. This provides significant advantages over prior art systems in which fittings between valves and columns are all cumbersome and take an undesirable amount of labor in order to change. With the present invention, different column configurations, and different valve configurations can be made to the gas chromatograph by simply unplugging and replacing module 16. This takes only a single wrench which is used to loosen the securing bolts securing locking bar 170. With the columns, the valves, the TCDs, and the heater, all in one module, the entire gas chromatograph module is very conveniently contained.

Further, it should be noted that all critical elements are together in a controlled thermal environment so that inaccuracies due to the high sensitivity of the system to temperature fluctuations are significantly reduced or eliminated.

All of the internal volumes of the system act as pressure capacitors which can result in pressure fluctuations. To alleviate or reduce problems, the manifold 128 of the present invention keeps the internal volumes very small so that any pressure bumps or fluctuations in the system are also very small and tail off very quickly. This allows the chromotographer to do chromatography more quickly. Further, the channels in the manifold and the tubing are very narrow (preferably on the order of 0.005 inch diameter) channels which also serves to reduce the internal volumes. The restricters in the flow paths simulate columns and further act to smooth out pressure bumps.

Although the present invention has been described with reference to preferred embodiments, workers skilled in the art will recognize that changes may be made in form and detail without departing from the spirit and scope of the invention.

What is claimed is:

1. A gas chromatograph, comprising:

a baseplate;

a valve module, comprising at least:

a manifold having a plurality of gas conduits formed therein, each gas conduit having an opening communicating therewith the manifold comprising:

a first plate having a plurality of apertures;

a second plate having a plurality of apertures;

a separating layer, connected between the first and second plates and separating the first and second plates to define voids comprising the gas conduits in the manifold, the voids communicating with the apertures in the first and second plates such that the apertures define the openings in the gas conduits; and wherein the separating layer is configured to allow for communication of electrical signals between the first and second plates;

a support;

a first valve mounted to the support and having a plurality of ports; and a column coupled to the support and being in communication with a port in the first valve;

wherein the valve module is pluggably engageable with the baseplate; and a detector coupled relative to the column to detect gases expelled from the column.

2. The gas chromatograph of claim 1 and further comprising:

a second valve mounted to the support and having a plurality of ports.

3. The gas chromatograph of claim 1 wherein the first actuated valve comprises a micromachined, multi-position valve.

4. The gas chromatograph of claim 1 and further comprising:

a plurality of tubes coupled between the first valve and the manifold carried by one of the baseplate and the valve module so that a valve port in the first valve communicates with an opening in a gas conduit formed in the manifold.

5. The gas chromatograph of claim 4 wherein the plurality of tubes are rigidly connected to the support and pluggably engage the openings in the manifold.

6. The gas chromatograph of claim 1 wherein the first valve is pluggably engageable with the support.

7. The gas chromatograph of claim 1 wherein the detector is mounted to the support and is pluggably engageable with the support.

8. The gas chromatograph of claim 7 wherein the valve module comprises a reference detector pluggably engageable with the support.

9. The gas chromatograph of claim 8 wherein the valve module comprises:

a heater in thermal contact with the column, the first valve, the detector, and the reference detector.

10. The gas chromatograph of claim 1 wherein the column is disposed proximate a periphery of the support.

11. The gas chromatograph of claim 10 wherein the support includes a spool having an inner periphery and an outer periphery and wherein a portion of the column is disposed within the inner periphery and is spring loaded against the inner periphery of the spool.

12. The gas chromatograph of claim 1 wherein:

the separating layer has at least one aperture for communication of electrical signals between the first and second plates.

13. The gas chromatograph of claim 1 wherein a first aperture in the first plate, conducting a gas sample to the first valve, is aligned with a first aperture in the second plate conducting the gas sample to the first valve.

14. The gas chromatograph of claim 13 wherein a second aperture in the first plate, conducting a gas sample away from the first valve, is aligned with a second aperture in the second plate conducting the gas sample away from the first valve.

15. The gas chromatograph of claim 2 wherein one of the first and second valves includes a carrier gas input port and a vent port and wherein the one of the valves selectively conducts a carrier gas between the carrier gas input port and one of the column and the vent port, and further including:

a vent valve communicating with the carrier gas input port controlling flow through the carrier gas input port to approximate flow through the column.

* * * * *